United States Patent [19]

Eckert

[11] Patent Number: 5,334,020
[45] Date of Patent: Aug. 2, 1994

[54] DENTAL PROPHYLAXIS CUP

[76] Inventor: Ronald C. Eckert, 4267 Sugar Maple La., Okemos, Mich. 48864

[21] Appl. No.: 741,737

[22] Filed: Aug. 7, 1991

Related U.S. Application Data

[63] Continuation-in-part of Ser. No. 608,340, Nov. 2, 1990, Pat. No. 5,178,538.

[51] Int. Cl.⁵ .......................... A61C 3/06; A61C 1/08
[52] U.S. Cl. ..................................... 433/166; 433/125
[58] Field of Search ................................ 433/166, 125

[56] References Cited

U.S. PATENT DOCUMENTS

| | | | |
|---|---|---|---|
| 1,620,990 | 3/1927 | Brothers . | |
| 1,644,465 | 10/1927 | Chott . | |
| 1,837,938 | 12/1931 | Young . | |
| 2,093,006 | 9/1937 | Chott . | |
| 2,093,007 | 9/1937 | Chott | 15/246 |
| 3,789,462 | 2/1974 | Reich | 32/59 |
| 3,977,083 | 8/1976 | Leslie et al. | 32/58 |
| 3,977,084 | 8/1976 | Sloan | 433/216 |
| 4,097,995 | 7/1978 | Danne et al. | 32/58 |
| 4,185,388 | 1/1980 | Jarby | 433/166 X |
| 4,259,071 | 3/1981 | Warden et al. | 433/166 |
| 4,266,933 | 5/1981 | Warden et al. | 433/82 |
| 4,544,356 | 10/1985 | Gardella et al. | 433/125 X |
| 4,601,561 | 7/1986 | Du Be' et al. | 433/134 |
| 4,636,171 | 1/1987 | Martin | 433/134 |
| 5,208,233 | 7/1991 | Witherby | 433/125 |

Primary Examiner—Gene Mancene
Assistant Examiner—Nicholas D. Lucchesi
Attorney, Agent, or Firm—Ian C. McLeod

[57] ABSTRACT

An improved prophylaxis cup (10) formed of a silicone elastomer incorporated with a pumice material (17) uniformly incorporated throughout the cup and mounted on a mounting button (11) in a non-disposable dental handpiece (110) is described. After a teeth cleaning procedure, the prophylaxis cup is disposed of and the mounting button and the dental handpiece are sterilized for reuse. The mounting button is comprised of a bulbous mounting head (23) having a circular cross-section that mates with a similarly shaped cavity (19) in a mounting section (13) of the cup. The cavity is preferably about 5 to 15 percent smaller in cross-sectional diameter than the mounting head so that the cup must be stretched over the mounted head for mounting the cup on the mounting button. A working section (15) of the cup is provided with a conical recess (15c) that wears down as the teeth are being cleaned to provide continuous application of fresh abrasive to the tooth surface. The prophylaxis cup mounted on a disposable dental handpiece or angled attachment (210) is also shown Further, the process for manufacturing the prophylaxis cup is described.

57 Claims, 3 Drawing Sheets

DENTAL PROPHYLAXIS CUP

CROSS-REFERENCE TO RELATED APPLICATION

This application is a continuation-in-part of my application Ser. No, 608,340 filed Nov. 2, 1990, now U.S. Pat. No. 5,178,538.

BACKGROUND OF THE INVENTION (1) Field of the Invention

The present invention relates to an improved dental prophylaxis (prophylactic) cup and method of use of the cup. In particular, the present invention relates to an improved dental prophylaxis cup that is molded from a medical grade silicone elastomer (flexible silicone polymer) incorporating an abrasive, preferably a coarse pumice material. The incorporated pumice is a dental cleaning and polishing agent and eliminates the need for applying any external cleaning paste to the prophylaxis cup.

(2) Prior Art

The prior art has described various types of devices for securing a cleaning device such as a dental prophylaxis cup to a dental handpiece. The dental handpiece is a mechanical instrument that is used to rotate the cup for the teeth cleaning procedure. Most of the prior art prophylaxis cups are formed from an elastomeric material, such as a rubber compound, Even when the working end of the cup is provided with a raised or ribbed configuration, the elastomeric cups alone are not particularly suited for cleaning stains and plaque from teeth and from within gingival crevices or sulci. To facilitate the cleaning process, an abrasive cleaning paste is required. The paste is applied to the prophylaxis cup by one of two methods. The most universally used method requires that the cup be dipped into a paste source to coat the working end of the prophylaxis cup with the paste. However, the paste is quickly worked off the prophylaxis cup and the cleaning paste must be frequently applied to the working end of the cup during the teeth cleaning. Illustrative to this type of device is U.S. Pat. Nos. 1,620,990 to Brothers; 1,644,465 to Chott; 1,837,938 to Young; 2,093,006 to Chott; 2,093,007 to Chott and 4,259,071 to Warden et al.

In the second method, which is not in service, the prophylaxis cup is provided with a central passage system for introducing a dental cleaning paste to the working end of the cup. The paste is stored in a storage compartment in the dental handpiece tool and is pumped through the passage system to the working end of the cup during the teeth cleaning procedure. The dental handpiece tool must then be sterilized between patients and the paste storage compartment must be periodically refilled with cleaning paste. Illustrative of this type of device is U.S. Pat. Nos. 3,977,083 to Leslie et al; 3,977,084 to Sloan; 4,097,995 to Danne et al and 4,266,933 to Warden et al.

The prior art has also shown rotatable discs with embedded abrasive material that are used for dental hygiene. Illustrative of this prior art is U.S. Pat. No. 4,601,661 to Du Be' et al.

U.S. Pat. No. 4,636,171 to Martin describes a polishing tip (FIG. 2) made of a silicone rubber material mounted on a mandrel driven by a dental engine. The polishing tip is described as being filled with an abrasive material such as aluminum oxide or zirconium flour, to produce a self-contained abrasive unit. In FIG. 3, Martin describes a polishing cup with a conical recess at a working end of the cup. The polishing cup does not contain an abrasive material, but instead requires a paste incorporating an abrasive. This signifies one of the problems overcome by the present invention. While silicone rubber polishing tips (FIG. 2) impregnated with an abrasive are known in the prior art, until the present invention, a silicone elastomeric prophylaxis cup incorporating an abrasive has not been invented. The reason for this is that it is difficult to mold an abrasive filled silicone elastomeric cup having a rim formed by a conical recess of the cup that will hold up during the teeth cleaning procedure. Also, the mandrel and dental engine have a straight construction along a longitudinal axis of the mandrel and engine and most tooth surfaces are inaccessible using this engine and polishing tip.

Finally, the prior art has described abrasive filled dental prophylaxis cups. U.S. Pat. No. 3,789,462 to Reich describes an abrasive-filled dental cup formed from a urethane elastomer. The polyurethane elastomer consists essentially of tolylene diisocyanate (TDI) endcapped polytetrahydrofuran cured with 4,4'-methylene bis(o-chloroaniline). The elastomer has 25–40 percent by weight of pumice added to the elastomer as a dental abrasive which obviates the use of a prophylaxis dental paste with the prophylaxis cup. The prophylaxis cup is formed as a shaped body molded on a mounting member comprised of a mandrel and a threaded shaft for removably mounting the cup on a dental handpiece and thus the design is different. The prophylaxis cup is not removeable from the mounting member. Polyurethanes are not suitable for use in the mouth. The precursors are suspected carcinogens as shown by the Merck Index 11th edition (1989) and any residual monomers would have the potential for toxicity.

There is therefore a need for a reliable dental prophylaxis cup for cleaning plaque and stains from teeth and gingival crevices or sulci that eliminates the need for a dental cleaning paste or material to be applied to the prophylaxis cup and which is removeably mounted on a "dental button member" in a dental handpiece. The prophylaxis cup of the present invention satisfies this need by providing a prophylaxis cup formed of a medical grade silicone elastomer, incorporating a coarse pumice as the cleaning agent. The pumice eliminates the need for a cleaning paste to be used during the teeth cleaning procedure which is a significant improvement over the prior art prophylaxis cups that require a dental cleaning paste. During the prophylaxis procedure, the paste will splatter. These extra-oral splatterings include blood and saliva which contain pathogenic, disease causing organisms. Thus, by eliminating dental cleaning paste, the prophylaxis cup of the present invention enhances infection and disease control for both the dentist or hygienist, and the patient. Rinsing is also eliminated. Elimination of splattering also increases the useful life of the dental handpiece because the pumice abrasive does not infiltrate into the gears of the handpiece to wear them.

OBJECTS

It is therefore an object of the present invention to provide an improved single use, dental prophylaxis cup formed of a non-toxic medical grade silicone elastomer, incorporating an abrasive for use in cleaning stains and plaque from teeth and from within gingival crevices or sulci. Further, it is an object of the present invention to provide an improved prophylaxis cup formed of an abrasive incorporated into a non-toxic silicone elastomer, that is removeably mounted on a dental handpiece for disposal of the prophylaxis cup and for sterilizing the dental handpiece after a prophylaxis procedure. Further, it is an object of the present invention to provide an abrasive incorporated into a non-toxic silicone elastomer prophylaxis cup mounted on a disposable dental handpiece section (called a prophylaxis angle attachment) as a unit which cup does not require any additional cleaning paste for cleaning stains and plaque from teeth and from within gingival crevices and which unit is completely disposed of after the teeth cleaning procedure. Still further, it is an object of the present invention to provide an improved dental prophylaxis cup formed of a non-toxic silicone elastomer incorporating an abrasive uniformly dispersed throughout so that both a polishing cavity in a working end of the cup can be used to clean teeth as well as the outside surface of the cup, thus enhancing operator convenience. Furthermore, it is an object of the present invention to provide a prophylaxis cup comprised of a silicone elastomer incorporating a pumice abrasive wherein the cup wears down during a teeth cleaning procedure to continuously apply fresh abrasive to the tooth surface without the abrasive splattering which significantly enhances infection control and patient satisfaction. Finally, it is an object of the present invention to provide an improved dental prophylaxis cup formed of a non-toxic, abrasive incorporated into a silicone polymer which is relatively simple and inexpensive to manufacture. Another object of the present invention is to increase patient acceptance and satisfaction by eliminating the sensation of grittiness within the mouth during and after the prophylaxis. These and other objects will become increasingly apparent by reference to the following descriptions and to the drawings.

GENERAL DESCRIPTION

The present invention relates to a flexible prophylaxis cup for cleaning teeth which is to be mounted on a dental handpiece including a holding portion of a holding member having a longitudinal axis and having a proximal end which is rotated by a rotating means of the dental handpiece and having a distal end and a head portion at the distal end of the holding portion along the longitudinal axis, the head portion having a reduced cross-section portion adjacent the distal end and enlarged cross-section portion extending from the reduced portion, the improvement in the prophylaxis cup which comprises: a silicone polymer with an abrasive material incorporated therein and having a shaped body adapted for cleaning teeth with a mounting end to be secured over the enlarged portion and over the reduced portion of the head portion and an opposite, working end around the longitudinal axis of the head portion, spaced from the mounting end, wherein the mounting end has an inletted portion that is smaller in cross-section than the enlarged portion and reduced portion of the head portion of the holding member so that when the prophylaxis cup is mounted on the holding member with the mounting end of the cup mounted on the head portion of the holding member, the inletted portion is stretched over the enlarged portion and the reduced portion in a friction fit that does not slip as the working end of the cup is used to clean teeth.

Further, the present invention relates to a flexible prophylaxis cup for cleaning teeth which is to be mounted on a dental handpiece including a holding portion of a holding member having a longitudinal axis and having a proximal end which is rotated by a rotating means of the dental handpiece and having a distal end, and a head portion at the distal end of the holding portion along the longitudinal axis, the head portion mounting an annular disc adjacent to the handpiece with a reduced cross-section portion adjacent the annular disc and with an enlarged cross-section portion extending from the reduced portion, the improvement in the prophylaxis cup which comprises: the prophylaxis cup adapted for cleaning teeth and comprised of a silicone polymer with an abrasive material incorporated therein and including a mounting end and a working end, the mounting end having a cavity along the longitudinal axis that is shaped similarly with the opposed end of the head portion of the holding member and which is smaller in cross-sectional diameter than the reduced portion and the enlarged portion of the head portion, wherein when the prophylaxis cup mounts on the head portion, the mounting end is adjacent to the annular disc, spaced from the dental handpiece and the cavity in the mounting end of the cup is in a friction fit with the reduced portion and the enlarged portion so that the cup does not slip on the head portion of the holding member when the working end of the cup is used to clean teeth.

Still further, the present invention relates to a dental handpiece including a holding portion of a holding member for mounting a dental prophylaxis cup, the holding portion having a longitudinal axis and having a proximal end which is rotated by a rotating means of the dental handpiece and having a distal end, and a head portion of the holding member at the distal end of the holding portion along the longitudinal axis, the head portion having a reduced cross-section portion adjacent the distal end of the holding portion and an enlarged cross-section portion spaced from the distal end, the improvement in the prophylaxis cup which comprises: a silicone polymer with an abrasive material incorporated therein and providing a shaped body adapted for cleaning teeth with a mounting end for securing the prophylaxis cup over the reduced portion and the enlarged portion of the head portion and an opposite working end around the longitudinal axis of the head portion, spaced from the mounting end, wherein the mounting end has an inletted portion that is similar in shape with the head portion of the holding member and is smaller in cross-section than the reduced portion and the enlarged portion of the head portion of the holding member so that when the prophylaxis cup is mounted on the holding member with the mounting end of the cup mounted on the head portion of the holding member, the inletted portion is stretched over the enlarged portion and the reduced portion in a friction fit that does not slip as the working end of the cup is used to clean teeth.

Furthermore, the present invention also relates to a method for cleaning teeth with a flexible prophylaxis cup which is to be mounted on a dental handpiece including a holding portion of a holding member having a longitudinal axis and having a proximal end which is rotated by a rotating means of the dental handpiece and a distal end and a head portion at the distal end of the holding portion along the longitudinal axis, the head portion having a reduced cross-section portion adjacent the distal end and an enlarged cross-section portion extending from the reduced portion, the improvement in cleaning teeth with the prophylaxis cup which comprises: providing the prophylaxis cup comprised of a silicone polymer with an abrasive material incorporated therein and having a shaped body adapted for cleaning teeth with a mounting end to be secured over the enlarged and reduced sections of the head portion and an opposite, working end around the longitudinal axis of the head portion, spaced from the mounting end, wherein the mounting end has an inletted portion that is smaller in cross-section than the enlarged portion and the reduced portion of the head portion of the holding member so that when the prophylaxis cup is mounted on the holding member with the mounting end of the cup mounted on the head portion of the holding member, the inletted portion is stretched over the enlarged section in friction fit that does not slip as the working end of the cup is used for prophylaxis; and cleaning the teeth with the prophylaxis cup while holding the dental handpiece.

Finally, the present invention relates to a method of cleaning plaque and stains from teeth and gingival crevices with a dental handpiece including a holding portion of a holding member for mounting dental prophylaxis cup, the holding portion having a longitudinal axis and having a proximal end which is rotated by a rotating means of the dental handpiece and having a distal end, and a head portion of the holding member at the distal end of the holding portion along the longitudinal axis, the head portion mounting an annular disc adjacent to the handpiece with a reduced cross-section portion adjacent to the annular disc and an enlarged cross-section portion extending from the reduced cross-section portion, the improvement in the prophylaxis cup which comprises: providing the prophylaxis cup comprised of a silicone polymer with an abrasive material incorporated therein and having a shaped body adapted for cleaning teeth with a mounting end for securing the prophylaxis cup over the reduced portion and the enlarged portion of the head portion and an opposite working end around the longitudinal axis of the head portion, spaced from the mounting end and wherein the mounting end has a cavity along the longitudinal axis that is similar in shape with the head portion of the holding member and is smaller in cross-section than the reduced portion and the enlarged portion of the head portion of the holding member so that when the prophylaxis cup is mounted on the holding member with the mounting end of the cup mounted on the head portion of the holding member, an end of the mounting end, spaced from the working end of the cup is mounted adjacent to the annular disc when the cavity is stretched over the enlarged portion and the reduced portion in a friction fit that does not slip as the working end of the cup is used for prophylaxis; and cleaning the teeth and gingival crevices with the prophylaxis cup while holding the dental handpiece.

Silicone elastomers as polymers are poorly adherent to any surface and are especially useful as water-resistant and heat-resistant lubricants. When an abrasive such as pumice is added to a silicone elastomer, the poor bonding characteristics of silicone are augmented. The inclusion of pumice not only increases the non-adherent properties of silicone elastomers, but it also degrades the high tensile strength silicone elastomers characteristically exhibit. On the other hand, silicone elastomers are very flexible polymers that tend to be extremely resilient. The prophylaxis cup of the present invention takes advantage of this inherent flexibility and is a molded silicone polymer member having a working end and a mounting end.

The mounting end of the prophylaxis cup is provided with a cavity that serves for mounting the cup on a "button" shaped holding member of a dental handpiece. The cavity has a cross-section that is similar in shape to that of the mounting end of the holding member. However, a corresponding cross-section of the cavity is preferably about 5 to 15 percent smaller than a cross-section of the mounting end of the holding member. This necessitates that the prophylaxis cup, as a silicone rubber, have elastic characteristics so that the mounting end of the cup will stretch and snap over the mounting end of the holding member. These elastic properties coupled with the incorporated pumice, keep the cup from slipping on the holding member during the teeth cleaning procedure. In this manner, the pumice abrasive helps to create a friction fit for the prophylaxis cup mounted on the holding member.

The holding member is secured to the dental handpiece in either a permanent or a removeable mounting. In the removeable mounting, the dental handpiece or disposable angle attachment is detached from an electric motor drive means and disposed of along with the prophylaxis cup after a single cleaning. In the permanent embodiment, the prophylaxis cup is removed and disposed of after the teeth cleaning procedure. The dental handpiece and the holding member are then sterilized before the next use.

The working end of the prophylaxis cup has a conical recess with the wide cross-section of the recess spaced from the mounting end. This way, during a teeth cleaning procedure, the sidewalls of the prophylaxis cup flare out to provide a greater surface area for cleaning and polishing teeth while the incorporated pumice acts as a gentle cleaning agent. This eliminates the need for a dentist or hygienist to have to continually apply a cleaning paste to the prophylaxis cup. The silicone polymer also acts as a lubricant which reduces heat build-up caused by the prophylaxis cup rubbing against the teeth. Instead, the pumice performs the cleaning with relatively little heat being created. The pumice abrasive can be evenly dispersed throughout the silicone elastomer forming both the mounting end and the working end of the prophylaxis cup, or the abrasive can be only incorporated in the working surfaces which include the end of the cup and the outside surfaces of the cup. The outside of the cup is a working surface and thus will contain the incorporated abrasive. Also, besides using the prophylaxis cup to clean stains and plaque from teeth and from within gingival crevices, the cup can be used to prepolish teeth in preparation for all types of acid-etch procedures including sealants, bonding and attaching orthodontic brackets.

The polymer material is preferably a silicone polymer. Medical grade silicone polymer manufactured by Dow Corning, Inc., Midland, Mich. This polymer is catalyzed with platinum rather than hydrogen peroxide which is used for most commercial applications. This is because platinum is more effective in reducing impurities than hydrogen peroxide. Other polymers are known and can be used if they are suitable for use in the mouth or for laboratory purposes. The polymer material preferably contains between 20 and 50 percent by weight of the abrasive material. The abrasive material for dental purposes can be pumice or pumice based powders, quartz and quartz based powders, zirconium silicate and zirconium silicate based powders and feldspar and feldspar based powders as specified by ANSI/ADA Specification to 37-1986. Type I up to 150 microns is for oral use and Type II up to 250 microns is for laboratory use such as on appliances and dentures. Type I is preferably between about 37 and 150 microns and Type II is preferably between about 74 and 250 microns.

The polymer material can be filled with medicament compounds such as sodium fluoride stannous fluoride and other fluoride containing compounds as anti-caries agents and/or strontium chloride or other tooth desensitizers and/or with flavorings, such as mint.

As used herein the term "cleaning" includes polishing, rubbing and the like. The term "cleaning" is used in its most generic sense. The cup can have a cone angle (alpha in FIG. 2) of between about 75° and 142°.

As a result of testing, an angle of 93° is preferred.

The prophylaxis cup can be mounted on a threaded mounting screw for threadably mating with the dental handpiece or the prophylaxis cup can be mounted onto a button which is then assembled into a dental handpiece (disposable angle attachment) as a disposable unit. Another embodiment of the present invention which is presently in use has a latch-type mechanical connection between the holding member and the dental handpiece. In the latch-type embodiment, the holding member has a groove formed in a shaft end of the holding member, opposite the prophylaxis cup. When the holding member is inserted into the dental handpiece, a releasable latch in the handpiece snaps into the groove and secures the prophylaxis cup into the dental handpiece. To release the prophylaxis cup, a release button on the dental handpiece is pushed. This retracts the retractable latch and releases the prophylaxis cup and holding member in a quick-release manner.

SPECIFIC DESCRIPTION

The following Example 1 shows the preferred method for the preparation of a prophylaxis cup 10.

EXAMPLE 1

In the preparation of the prophylaxis cup 10, 40 parts pumice and 100 parts silicone polymer are used (Dow Corning Q7-4765 and Q7-4750 in equal parts referred to as parts A and B). The pumice and silicone are mixed in a two roll mill, half of the pumice with part A and half the pumice with part B. The parts A and B, are then combined and milled cold (refrigeration temperatures). The mixture is stored at refrigeration temperatures prior to use only a sufficient amount of material to be molded within four (4) hours is removed from refrigeration.

Figure 1:
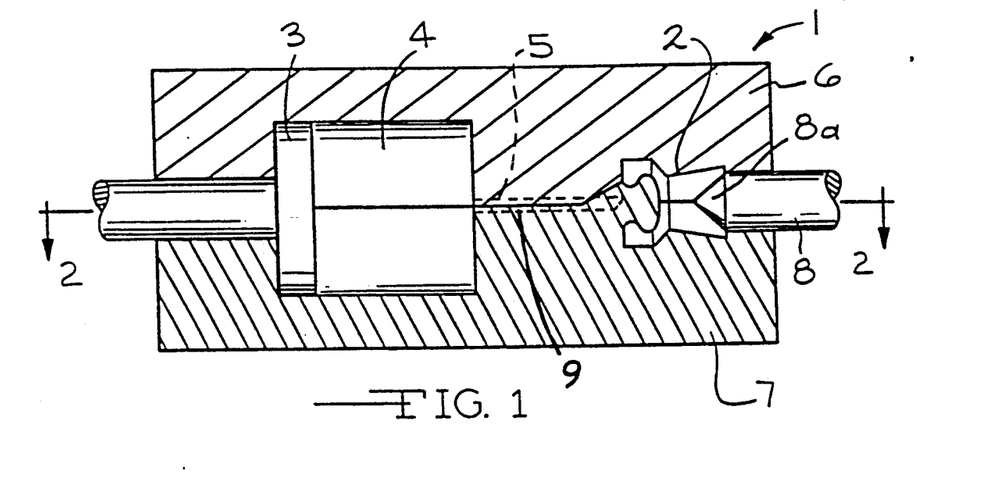
FIG. 1 is a cross-sectional view of a transfer press 1 for molding a prophylaxis cup 10 (not shown in FIG. 1) in mold cavities 2 formed between mold platens 6 and 7.
Figure 2:
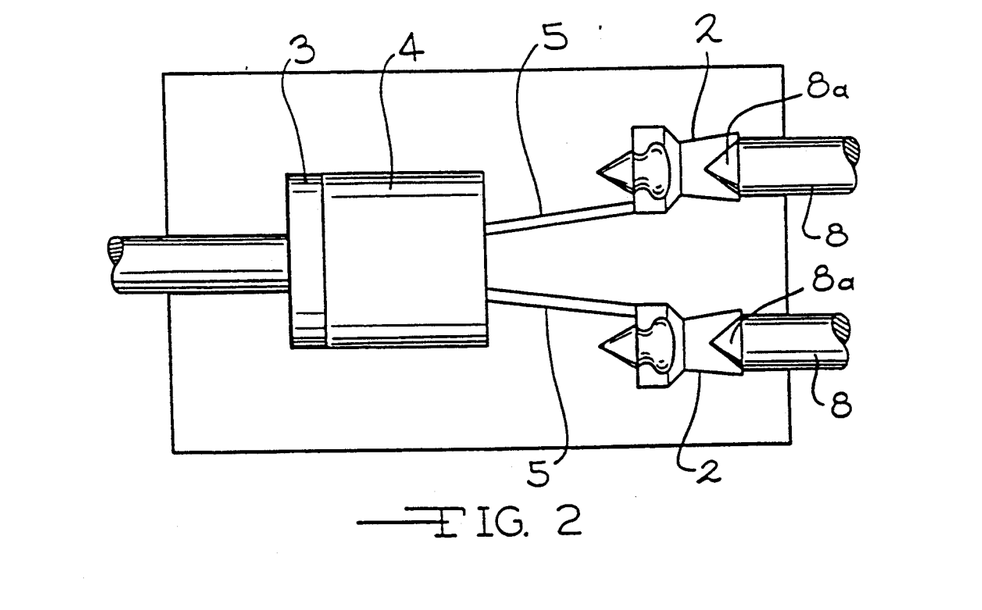
FIG. 2 is a cross-sectional view along line 2—2 of FIG. 1 showing mold cavities 2 in communication with a reservoir 4 having a piston injector 3 (shown in an up stroke position) for injecting a silicone polymer material incorporated with pumice from the reservoir into the mold cavities 2.
Figures 3, 4:
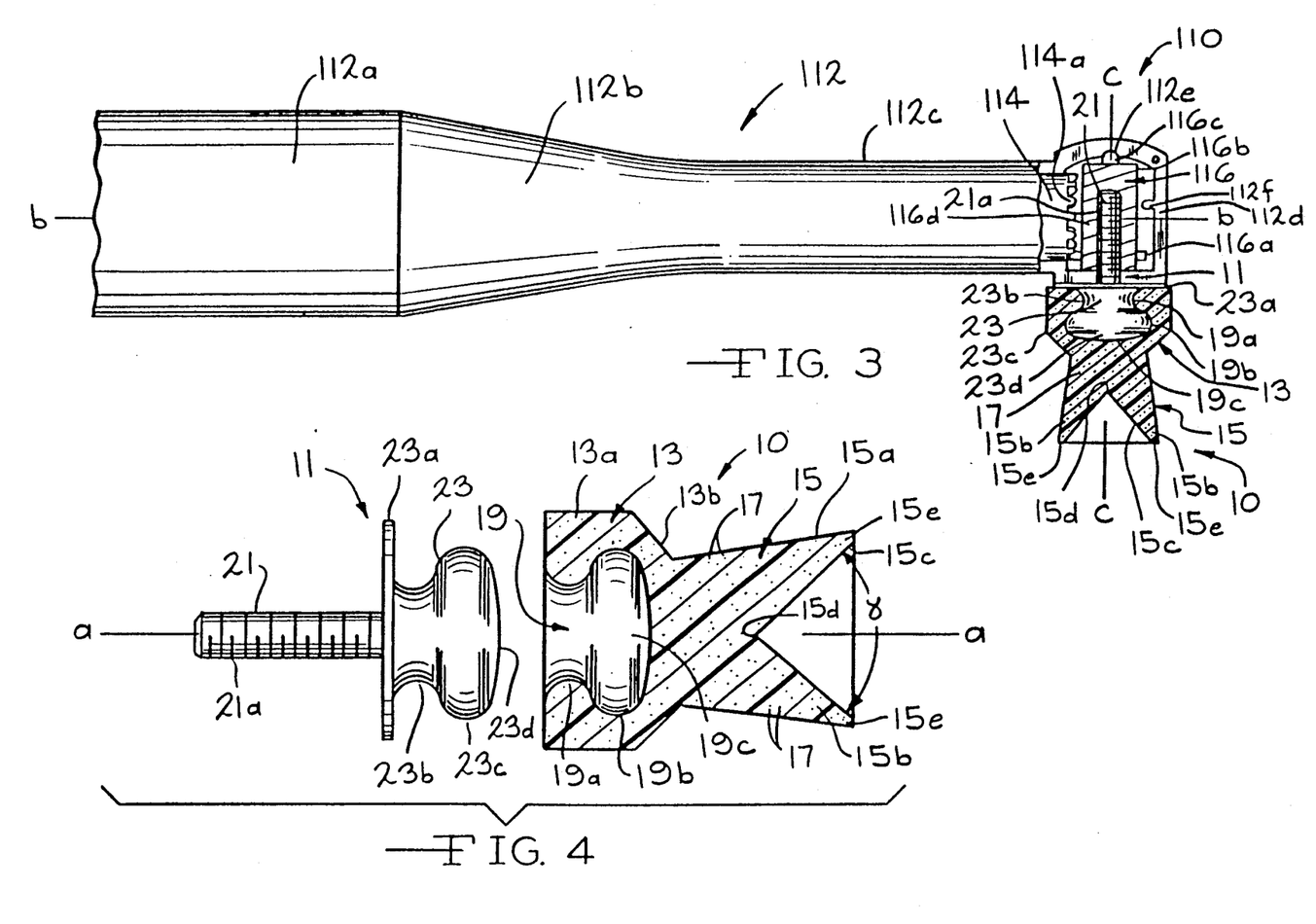
FIG. 3 is a partial side view with a portion in cross-section of the prophylaxis cup 10 mounted on a mounting button 11 which is threadably mated to a secondary drive shaft 116 of a non-disposable dental handpiece 110.
FIG. 4 is an isometric, separated view of the prophylaxis cup 10 and the mounting button 11.

As shown in FIGS. 1 and 2, the molding is accomplished in a transfer press 1 having mold cavities 2 for the prophylaxis cup 10. The press 1 has a piston injector 3 (shown in an up stroke position) connected to a reservoir 4 for injecting the silicone polymer through passages 5 in communication with the mold cavities 2 in mold platens 6 and 7. A removeable die 8 having a conical head 8a is mounted between the platens 6 and 7 and connects with the cavities 2 to form the prophylaxis cup 10 (not shown in FIGS. 1 and 2). The silicone polymer injected into the cavities 2 is heated to 370° F. (187.8° C.) for 4 minutes at 2000 psi (146 kg/sq meter) transfer. Pressure on the piston 3 from the reservoir 4 is for 40 seconds. Platens 6 and 7 are cross ground at 90° angles to each other to allow for venting of air and silicone polymer at the union 9 between the platens 6 and 7, thus allowing the mold cavities 2 to be completely filled with silicone polymer. The charging pressure on the platens 6 and 7 was 16,000 psi (168 kg/sq. meter). The molding time is between about 1 and 5 minutes, preferably 3 minutes. Following removal From the platens 6 and 7, the prophylaxis cup 10 was then post cured at 325° F. (162.80° C.) for 1 hour, The prophylaxis cup 10 had a hardness of 64 Durometer on the "A" scale. A release agent was not used in the method.

The post curing at elected temperatures is necessary to provide the proper resiliency to the prophylaxis cup 10, Preferably the post cure was at least 50 to 75 Durometer as achieved. Usually this is at a temperature between about 300° F. to 370° F. (148.9° C. to 187.8° C.).

Figures 5, 6:
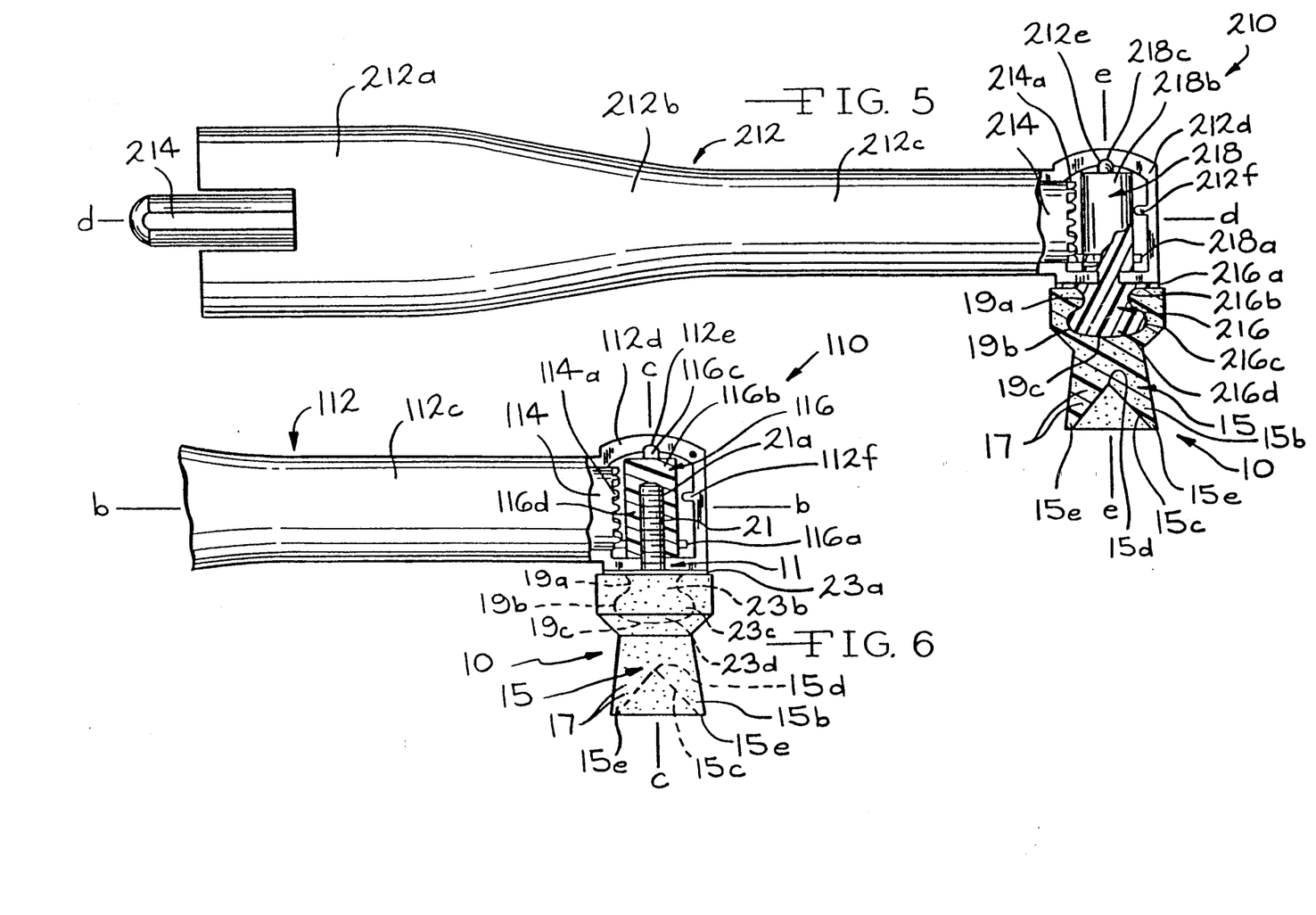
FIG. 5 is a side view with a portion in cross-section of the prophylaxis cup 10 mounted on a mounting button member 216 of a disposable dental handpiece 210.
FIG. 6 is a partial side view with a portion in cross-section of the prophylaxis cup 10 mounted on the mounting button 11 which is threadably mated to the non-disposable dental handpiece 110.

A preferred embodiment of the dental prophylaxis cup device 10 molded by the above described process is shown in FIGS. 3 to 6. The prophylaxis cup 10 mounts on a mounting button member 11 as a holding member for using the prophylaxis cup 10 with a non-disposable dental handpiece or instrument 110 as shown in FIGS. 3 and 6 and a disposable dental handpiece 210 as shown in FIG. 5. The prophylaxis cup 10 is then used to clean and polish teeth and gingival crevices.

The prophylaxis cup 10 is a molded member formed from a silicone elastomer. The cup 10 is comprised of a mounting section 13 and a working section 15. The mounting section 13 has a cylindrical portion 13a having a circular cross-section along and around a longitudinal axis a—a of the cup 10, as shown in FIG. 4, The cylindrical portion 13a extends to a frusto-conical portion 13b that tapers inwardly along the axis a—a from the cylindrical portion 13a to the working section 15 of the cup 10. The working section 15 has a frusto-conical portion 15a that tapers outwardly along the axis a—a from the frusto-conical portion 13b of the mounting section 13 to an end 15b of the working section 15. The taper of the portion 13b is preferably somewhat greater than that of the portion 15a of the working section 15.

The prophylaxis cup 10 is mounted on the mounting button member 11 in an internal mounting cavity 19 provided in the mounting section 13 of the cup 10. The mounting cavity 19 has a circular cross-section along and around the axis a—a and is comprised of a convex annular portion 19a merging with a concave annular portion 19b that extends to a rounded end 19c of the mounting cavity 19.

The mounting button member 11 is a rigid member that serves for mounting the prophylaxis cup 10 on the dental handpiece 110. The mounting button 11 is comprised of a shaft 21 and a bulbous mounting head or button 23. As shown in detail in FIG. 4, the shaft 21 has a circular cross-section along the axis a—a and is preferably provided with threads 21a or other holding means (not shown) along and around the axis a—a for removably mounting the cup 10 and the button member 11 on the non-disposable dental handpiece 110 (FIG. 3). The threaded shaft 21 extends to the mounting head 23 which is comprised of a disc portion 23a with a concave annular portion 23b extending from an inner radius of the disc portion 23a. The concave annular portion 23b merges with a convex annular portion 23c that extends to a rounded end 23d of the mounting head 23. The general contour of the mounting cavity 19 is similar to that of the mounting head 23 except for the disc portion 23a. However, the mounting cavity 19 is about 5 to 15 percent smaller in comparable cross-section diameter than that of the mounting head 23. This allows the mounting section 13 of the cup 10 to mount on the mounting head 23 of the mounting screw 11 by stretching the cavity 19 over the mounting head 23 in a closely spaced relationship.

As shown in FIG. 4, the working section 15 of the prophylaxis cup 10 provides for a conical recess 15c that tapers inwardly from the end 15b of the working section 15 towards the axis a—a and towards the mounting section 13 of the cup 10. An apex 15d of the recess 15c is on the axis a—a, spaced from the mounting cavity 19 in the mounting section 13 of the cup 10. The end 15b of the working section 15 is radially larger than the base of the recess 15c, thereby forming a shoulder 15e at the end 15b of the cup 10. The shoulder 15e gives the cup 10 increased strength at the working section 15 and allows the recess 15c to be used either with or without a dental cleaning paste for cleaning teeth and gingival crevices when the prophylaxis cup 10 is rotatably mounted onto a dental handpiece as shown in FIGS. 3, 5 and 6.

The prophylaxis cup 10 does not slip on the mounting head 23 during the teeth cleaning procedure because the cup 10 is molded to the specifications previously described. Although silicone bonds poorly to any material, the silicone elastomer prophylaxis cup 10 of the present invention stretches over the mounting head 23 and holds in a no-slip, friction fit relationship. This prevents slippage between the cup 10 and the mounting screw 11 during the teeth cleaning procedure.

FIG. 3 shows a preferred non-disposable dental handpiece 110 supporting a prophylaxis cup 10 mounted on the mounting button member 11. The prophylaxis cup 10 is only used for a single teeth cleaning procedure. After the teeth cleaning, the prophylaxis cup 10 is properly disposed of and the handpiece 110 and mounting button 11 are sterilized for future use. During the sterilization procedure, the mounting button 11 is unthreaded from the dental handpiece 110 to ensure that the entire mounting button 11, including the threads 21a is properly sterilized. After sterilizing, the mounting button 11 is re-threaded into the handpiece 110 and another prophylaxis cup 10 is mounted in the button 11 for a subsequent teeth cleaning procedure.

The dental handpiece 110 is comprised of an elongated main body 112 having a primary drive shaft 114 mounting a secondary drive shaft 116. The main body 112 has a generally circular cross-section along the axis b—b with an enlarged proximal end 112a for holding by a dentist or a hygienist, a tapered intermediate section 112b and a distal end 112c extending to an angled head 112d housing the secondary drive shaft 116. The dental handpiece 110 is a molded device, preferably formed of a metal material that is readily sterilized. As shown in partial cut away view in FIGS. 3 and 6, the dental handpiece 110 is provided with the primary drive shaft 114 (only partially shown in the Figures) and the secondary drive shaft 116. The primary drive shaft 114 is provided with a cogwheel 114a. An opposite end of the drive shaft 114 is attached to a conventional electric motor (not shown) for providing a torque to the shaft 114.

The cogwheel 114a meshes with a gear wheel 116a on the secondary drive shaft 116. The gear wheel 116a changes the direction of the torque of the primary drive shaft 114 to the axis c—c of the secondary drive shaft 116, which is perpendicular to the axis b—b. A proximal end 116b of the secondary shaft 116 has an annular locating tab 116c along the axis c—c that mates with a locating recess 112e in the dental handpiece 110. A stabilizing tab 112f also helps to maintain the rotation of the secondary drive shaft 116 along the axis c—c. The disc portion 23a of the mounting head 23 of the mounting button 11 is provided between the prophylaxis cup 10 and the dental handpiece 110 and acts as a washer to prevent the cup 10 from rubbing on the handpiece 110 during the teeth cleaning procedure. The prophylaxis cup 10 also has a tendency to torque off of the mounting button 11 during the teeth cleaning procedure. However, the disc portion 23a is important because it prevents this from happening. As shown in FIGS. 3 and 6, an end of the secondary drive shaft 116, spaced from the locating tab 116c, has a threaded recess 116d that provides for threadably mating with the threads 21a on the shaft 21 of the mounting screw 11.

The dental handpiece 110 shown in FIGS. 3 and 6 can also be made of a plastic material as a disposable dental handpiece. In this embodiment, both the dental handpiece 110 and the threaded mounting button member 11 are made of a plastic material. Then after a teeth cleaning procedure, the prophylaxis cup 10 is properly disposed of along with the mounting button 11 and the dental handpiece 110. The dental handpiece 110 can also be made of a reinforced polymer composite material.

FIG. 5 shows a disposable dental handpiece that is similar to the non-disposable dental handpiece 110 in FIGS. 3 and 6, except that handpiece 210 is preferably made of an easily disposable material such as a plastic material. The dental handpiece 210 can also be made of a reinforced polymer composite material. Dental handpiece 210 is comprised of an elongated main body 212 (disposable angle attachment) having a primary drive shaft 214 mounting a unit formed by a mounting button member 216 and a secondary drive shaft 218. The main body 212 has a generally circular cross-section along the axis d—d with an enlarged holding end 212a, a tapered intermediate section 212b and a distal end 212c extending to an angled head 212d housing the button member 216 and secondary drive shaft 218. The primary drive shaft 214 (only partially shown in FIG. 5) runs the length of the handpiece 212. The drive shaft 214 provides for transmitting torque to the unit formed by the mounting button member 216 and the secondary drive shaft 218 from an external electric motor (not shown). The electric motor is a non-disposable prime mover means that attaches to the drive shaft 214 at the holding end 212a of the main body 212. A cogwheel 218a of the drive shaft 218 meshes with a geared wheel 214a on the primary drive shaft 214 for redirecting the torque of the primary shaft 214 to the axis e—e of the secondary drive shaft 218, perpendicular to the axis d—d of the drive shaft 214. A proximal end 218b of the secondary drive shaft 218 has an annular locating tab 218c along the axis e—e, that mates with a locating recess 212e in the angled head 212d of the main body 212 of the dental handpiece 210. A stabilizing tab 212f in the angled head 212d also helps to maintain the rotation of the secondary drive shaft 218 along the axis e—e.

The mounting button member 216 is formed as an integral unit with the secondary drive shaft 218 and provides for mounting the prophylaxis cup 10. The mounting button member 216 is similar to the mounting head 23 of the mounting button 11 (FIG. 4) and has a circular cross-section along and around the axis e—e. The mounting button member 216 is comprised of a disc portion 216a with a concave annular portion 216b extending from an inner radius of the disc portion 216a. The concave annular portion 216b merges with a convex annular portion 216c that extends to a rounded end 216d of the mounting button member 216. Except for the disc portion 216a, the general contour of the mounting button member 216 is similar to that of the mounting cavity 19 of the prophylaxis cup 10. However, a corresponding cross-section of the mounting cavity 19 is preferably about 5 to 15 percent smaller in cross-sectional diameter than that of the concave portion 216b, the convex portion 216c and the rounded end 216d of the mounting button member 216. This provides for the mounting section 13 of the cup 10 to securely mount on the mounting button member 216 in a stretched relationship. The disc portion 216a helps to prevent the prophylaxis cup 10 from rubbing on the handpiece 210 and from torquing off of the mounting button member 216 during the teeth cleaning process.

IN OPERATION

In operation, the prophylaxis cup 10 with the dental handpiece 110 in FIGS. 3 and 6 and the prophylaxis cup 10 with the dental handpiece 210 in FIG. 5 are used to clean teeth and gingival crevices of plaque and stains. Since the prophylaxis cup 10 is molded from a silicone material with an abrasive such as pumice 17 incorporated throughout, there is no need to apply a dental paste in association with the prophylaxis cup 10. After completion of the teeth cleaning procedure, the dentist or hygienist disposes of the prophylaxis cup 10. In the case of the non-disposable dental handpiece 110 in FIGS. 3 and 6, the dental handpiece 110 and the mounting button 11 are disassembled, sterilized, reassembled and another prophylaxis cup 10 is mounted on the button 11 for another teeth cleaning procedure. In the case of the disposable dental handpiece 210 in FIG. 5, the prophylaxis cup 10 and the dental handpiece 210 including the main body 212 (disposable angle attachment), the drive shaft 214 and the unit formed by the mounting button member 216 and the secondary drive shaft 218 are detached from the electric motor mean (not shown) and disposed of after a teeth cleaning procedure. This greatly enhances the infection control of the teeth cleaning procedure and reduces the risk of pathogenic organisms being passes from one patient to another. It also saves the time and cost that is normally required to sterilize a dental handpiece 210.

The conical recess in the working section 15 of the prophylaxis cup 10 is uniquely shaped to provide maximal contact of the flexible silicone polymer with the tooth surface. In use, the working section 15 of the cup 10 wears down providing continuous application of fresh abrasive to the tooth surface. In addition, the frusto-conical portion 13b of the mounting section 13 and the frusto-conical portion 15a of working section 15 are uniquely shaped. That way, the outside surfaces of the portions 13b and 15a can be used by a dentist or hygienist for polishing and cleaning the teeth, for example especially the lingual surfaces of the anterior teeth. The natural saliva present in the mouth is sufficient to wet the teeth for polishing or other procedures.

It is intended that the foregoing descriptions only be illustrative of the present invention and that the invention is only limited by the hereinafter appended claims.

I claim:

1. In a flexible prophylaxis cup for cleaning teeth which is to be mounted on a dental handpiece including a holding portion of a holding member having a longitudinal axis and having a proximal end which is rotated by a rotating means of the dental handpiece and having a distal end and a head portion at the distal end of the holding portion along the longitudinal axis, the head portion having a reduced cross-section portion adjacent the distal end and an enlarged cross-section portion extending from the reduced portion, the improvement in the prophylaxis cup, which comprises:

(a) a silicone polymer with an abrasive material incorporated therein, which has been heated and then injection molded to form the prophylaxis cup, wherein the cup is then post cured by heating to achieve a hardness between about 50 to 75 Durometer on the "A" scale, and wherein the prophylaxis cup has a shaped body adapted for cleaning teeth with a mounting end to be secured over the enlarged portion and over the reduced portion of the head portion of the holding member, and an opposite, working end around the longitudinal axis of the head portion, spaced from the mounting end, wherein the mounting end of the cup has an inletted portion that is smaller in cross-section than the enlarged portion and reduced portion of the head portion of the holding member so that when the prophylaxis cup is mounted on the holding member with the mounting end of the cup mounted on the head portion, the inletted portion is stretched over the enlarged portion and the reduced portion in a friction fit that does not slip as the working end of the cup is used to clean teeth.

2. The prophylaxis cup of claim 1 wherein the abrasive material is a pumice.

3. The prophylaxis cup of claim 2 wherein the pumice is between about 20 and 50 percent by weight of the cup material.

4. The prophylaxis cup of claim 1 wherein the working end of the cup has an opening in the shape of a cone with an apex angle between about 75° and 142° so that the cup can be used without a dental paste for polishing teeth.

5. The prophylaxis cup of claim 1 wherein a flavoring is present in the silicone polymer.

6. The prophylaxis cup of claim 1 wherein the abrasive material is evenly incorporated throughout the silicone polymer.

7. The prophylaxis cup of claim 1 wherein the abrasive material is incorporated into the working end of the prophylaxis cup.

8. The prophylaxis cup of claim 1 incorporating a medicament for the teeth.

9. The prophylaxis cup of claim 1 wherein the post cure has been performed outside of the mold.

10. The prophylaxis cup of claim 1 wherein when the cup is injection molded, the silicone polymer with the abrasive material incorporated therein is heated under pressure.

11. In a flexible prophylaxis cup for cleaning teeth which is to be mounted on a dental handpiece including a holding portion of a holding member having a longitudinal axis and having a proximal end which is rotated by a rotating means of the dental handpiece and having a distal end, and a head portion at the distal end of the holding portion along the longitudinal axis, the head portion mounting an annular disc adjacent to the handpiece with a reduced cross-section portion adjacent the annular disc and with an enlarged cross-section portion extending from the reduced portion, the improvement in the prophylaxis cup, which comprises:

(a) the prophylaxis cup adapted for cleaning teeth and comprised of a silicone polymer with an abrasive material incorporated therein, which has been heated and then injection molded to form the prophylaxis cup, wherein the cup is then post cured by heating to achieve a hardness between about 50 to 75 Durometer on the "A" scale, and wherein the prophylaxis cup includes a mounting end and a working end, the mounting end having a cavity along the longitudinal axis that is shaped similarly with the opposed end of the head portion of the holding member and which is smaller in cross-sectional diameter than the reduced portion and the enlarged portion of the head portion, wherein when the prophylaxis cup is mounted on the head portion of the holding member, the mounting end of the cup is adjacent to the annular disc, spaced from the dental handpiece and, the cavity in the mounting end of the cup is in a friction fit with the reduced portion and the enlarged portion of the head portion so that the cup does not slip on the head portion of the holding member when the working end of the cup is used to clean teeth.

12. The prophylaxis cup of claim 11 wherein the reduced portion and the enlarged portion of the head portion of the holding member have a circular cross-section perpendicular to the longitudinal axis and wherein the cavity in the mounting end has a circular cross-section perpendicular to the longitudinal axis.

13. The prophylaxis cup of claim 12 wherein the cavity in the mounting end of the prophylaxis cup is between about 5 and 15 percent smaller than the circular cross-sections of the reduced portion and the enlarged portion of the head portion.

14. The prophylaxis cup of claim 11 wherein the abrasive material has a particle size between 37 and 250 microns.

15. The prophylaxis cup of claim 11 wherein the abrasive material has a concentration of between 20 and 50 percent.

16. The prophylaxis cup of claim 11 wherein the abrasive material is pumice.

17. The prophylaxis cup of claim 11 wherein the abrasive material is evenly incorporated throughout the silicone polymer.

18. The prophylaxis cup of claim 11 wherein the abrasive material is incorporated into the working end of the prophylaxis cup.

19. The prophylaxis cup of claim 11 wherein the annular disc is an integral member of the head portion of the holding member.

20. The prophylaxis cup of claim 11 wherein the annular disc is a washer means mounted on the head portion of the holding member between the distal end of the holding portion and the reduced portion of the head portion of the holding member.

21. The prophylaxis cup of claim 11 wherein the post cure has been performed outside of the mold.

22. The prophylaxis cup of claim 11 wherein when the cup is injection molded, the silicone polymer with the abrasive material incorporated therein is heated under pressure.

23. In a dental handpiece including a holding portion of a holding member for mounting a dental prophylaxis cup, the holding portion having a longitudinal axis and having a proximal end which is rotated by a rotating means of the dental handpiece and having a distal end, and a head portion of the holding member at the distal end of the holding portion along the longitudinal axis, the head portion having a reduced cross-section portion adjacent the distal end of the holding portion and an enlarged cross-section portion extending from the reduced portion, the improvement in the prophylaxis cup, which comprises:

(a) a silicone polymer with an abrasive material incorporated therein, which has been heated and then injection molded to form the prophylaxis cup, wherein the cup is then post cured by heating to achieve a hardness between about 50 to 75 Durometer on the "A" scale, and wherein the prophylaxis cup has a shaped body for cleaning teeth with a mounting end for securing the prophylaxis cup over the reduced portion and the enlarged portion of the head portion of the holding member and an opposite, working end around the longitudinal axis of the head portion, spaced from the mounting end, wherein the mounting end has an inletted portion that is similar in shape with the head portion of the holding member and is smaller in cross-section than the reduced portion and the enlarged portion of the head portion of the holding member so that when the mounting end of the prophylaxis cup is mounted on the head portion of the holding member, the inletted portion is stretched over the enlarged portion and the reduced portion in a friction fit that does not slip as the working end of the cup is used to clean teeth.

24. The dental handpiece of claim 23 wherein the abrasive material is a pumice.

25. The dental handpiece of claim 24 wherein the pumice is between about 20 and 50 percent by weight of the cup material.

26. The dental handpiece of claim 23 wherein the holding portion is part of a disposable angle attachment for the dental handpiece which is provided with mating angle gears and a housing that supports the holding portion and the mating angle gears and wherein the mating angle gears accomplish a change in the direction of the torque of the dental handpiece with one of the gears provided adjacent to the proximal end of the holding portion of the holding member.

27. The dental handpiece of claim 26 wherein the gears, housing and holding member are all comprised of a plastic material.

28. The dental handpiece of claim 26 wherein some of the gears, housing and holding member are comprised of a metal material.

29. The dental handpiece of claim 26 wherein some of the gears, housing and holding member are comprised of a composite material.

30. The dental handpiece of claim 23 wherein the abrasive material has a particle size between 37 and 250 microns.

31. The dental handpiece of claim 23 wherein a flavoring is present in the silicone polymer.

32. The dental handpiece of claim 23 incorporating a medicament for the teeth.

33. The dental handpiece of claim 23 wherein the abrasive material has a concentration of between 20 and 50 percent.

34. The dental handpiece of claim 23 wherein the reduced portion and the enlarged portion of the head portion have a circular cross-section perpendicular to the longitudinal axis and wherein the inletted portion in the mounting end of the cup has a shape similar to that of the head portion of the holding member with a circular cross-section perpendicular to the longitudinal axis that is between about 5 and 15 percent smaller than a corresponding cross-section of the reduced so that the inletted portion in the mounting end of the cup stretches over the reduced and enlarged portions of the head portion.

35. The dental handpiece of claim 23 wherein the holding portion of the holding member is a threaded member comprised of the proximal end, which threads into a rotating member of the handpiece, and the distal end.

36. The dental handpiece of claim 23 wherein the abrasive material is evenly incorporated throughout the silicone polymer.

37. The dental handpiece of claim 23 wherein the abrasive material is incorporated into an outside surface of the cup.

38. The dental handpiece of claim 23 wherein the post cure has been performed outside of the mold.

39. The dental handpiece of claim 23 wherein when the cup is injection molded, the silicone polymer with the abrasive material incorporated therein is heated under pressure.

40. A method for cleaning teeth with a flexible prophylaxis, cup which is to be mounted on a dental handpiece including a holding portion of a holding member having a longitudinal axis and having a proximal end which is rotated by a rotating means of the dental handpiece and a distal end, and a head portion at the distal end of the holding portion along the longitudinal axis, the head portion having a reduced cross-section portion adjacent the distal end and an enlarged cross-section portion extending from the reduced portion, the improvement in cleaning teeth with the prophylaxis cup, which comprises:
(a) mounting the prophylaxis cup comprised of a silicone polymer with an abrasive material incorporated therein, which has been heated and then injection molded to form the prophylaxis cup, wherein the cup is then post cured by heating to achieve a hardness between about 50 to 75 Durometer on the "A" scale, and wherein the prophylaxis cup has a shaped body for cleaning teeth with a mounting end to be secured over the enlarged and reduced portions of the head portion and opposite, working end around the longitudinal axis of the head portion, spaced from the mounting end, wherein the mounting end has an inletted portion that is smaller in cross-section than the enlarged portion of the reduced portion of the head portion of the holding member, wherein when the mounting end of the prophylaxis cup is mounted on the head portion of the holding member, the inletted portion is stretched over the enlarged portion in a friction fit that does not slip as the working end of the cup is used for prophylaxis; and
(b) cleaning the teeth with the prophylaxis cut while holding the dental handpiece.

41. The method of claim 40 wherein a flavoring is present in the silicone polymer.

42. The method of claim 40 wherein a medicament is incorporated in the silicone polymer.

43. The method of claim 40 wherein the the abrasive is a coarse material having a particle size between about 37 and 250 microns and wherein the working end of the cup has an opening in the shape of a cone with an angle between about 75° and 142° so that the cup polishes the teeth and wherein the reduced portion and the enlarged portion of the head portion have circular cross-sections perpendicular to the longitudinal axis and wherein the inletted portion in the mounting end of the cup has a circular cross-section perpendicular to the longitudinal axis that is between about 5 and 15 percent smaller than the circular cross-section of a corresponding cross-section of the reduced portion and the enlarged portion of the head portion so that the inletted portion in the mounting end of the cup stretches over the reduced portion and the enlarged portion of the head portion of the holding member.

44. The method of claim 40 wherein the abrasive material is evenly incorporated throughout the silicone polymer.

45. The method of claim 40 wherein the abrasive material is incorporated into an outside surface of the prophylaxis cup.

46. The method of claim 40 wherein the post cure has been performed outside of the mold.

47. The method of claim 40 wherein when the cup is injection molded, the silicone polymer with the abrasive material incorporated therein is heated under pressure.

48. A method for cleaning plaque and stains from teeth and gingival crevices with a dental handpiece including a holding portion of a holding member for mounting a dental prophylaxis cup, the holding portion having a longitudinal axis and having a proximal end which is rotated by a rotating means of the dental handpiece and having a distal end, and a head portion of the holding member at the distal end of the holding portion along the longitudinal axis, the head portion mounting an annular disc adjacent to the handpiece with a reduced cross-section portion adjacent the annular disc and an enlarged cross-section portion extending from the reduced portion, the improvement in the prophylaxis cup, which comprises:
(a) mounting the prophylaxis cup comprised of a silicone polymer with an abrasive material incorporated therein, which has been heated and then injection molded to form the prophylaxis cup, wherein the cup is then post cured by heating to achieve a hardness between about 50 to 75 Durometer on the "A" scale, and wherein the prophylaxis cup has a shaped body for cleaning teeth with a mounting end to be securing the prophylaxis cup over the reduced portion and the enlarged portion of the head portion and an opposite working end around the longitudinal axis of the head portion, spaced from the mounting end, and wherein the mounting end has a cavity along the longitudinal axis that is similar in shape with the head portion of the holding member and is smaller in cross-section than the reduced portion and the enlarged portion of the head portion of the holding member so that when the mounting end of the prophylaxis cup is mounted on the head portion of the holding member, an end of the mounting end of the cup, spaced from the working end of the cup, is mounted adjacent to the annular disc when the cavity is stretched over the enlarged portion and the reduced portion of the head portion in a friction fit that does not slip as the working end of the cup is used for prophylaxis; and (b) cleaning the teeth and gingival crevices with the prophylaxis cup while holding the dental handpiece.

49. The method of claim 48 wherein the silicone polymer is filled with a coarse abrasive as the abrasive material having a particle size between about 37 and 250 microns and wherein the working end of the cup has an opening in the shape of a cone with an angle between about 75° and 142° so that the cup polishes the teeth and wherein the reduced portion and the enlarged portion of the head portion have circular cross-sections perpendicular to the longitudinal axis, and wherein the cavity in the mounting end of the cup has a circular cross-section perpendicular to the longitudinal axis that is between about 5 and 15 percent smaller than a corresponding cross-section of the reduced portion and the enlarged portion of the head portion so that the cavity in the mounting end of the cup stretches over the reduced portion and the enlarged portion of the head portion of the holding member.

50. The method of claim 48 wherein a flavoring is present in the silicone polymer.

51. The method of claim 48 wherein a medicament is incorporated in the silicone polymer.

52. The method of claim 48 wherein the abrasive material is evenly incorporated throughout the silicone polymer.

53. The method of claim 48 wherein the abrasive material is incorporated into an outside surface of the prophylaxis cup.

54. The method of claim 48 wherein the annular disc is an integral member of the head portion of the holding member.

55. The method of claim 48 wherein the annular disc is a washer means mounted on the head portion of the holding member between the distal end of the holding portion and the reduced portion of the head portion of the holding member.

56. The method of claim 48 wherein the post cure has been performed outside of the mold.

57. The method of claim 48 wherein when the cup is injection molded, the silicone polymer with the abrasive material incorporated therein is heated under pressure.

* * * * *

UNITED STATES PATENT AND TRADEMARK OFFICE
CERTIFICATE OF CORRECTION

PATENT NO. : 5,334,020  
DATED : August 2, 1994  
INVENTOR(S) : Ronald C. Eckert Page 1 of 2

It is certified that error appears in the above—identified patent and that said Letters Patent is hereby corrected as shown below:

Column 1, line 43, "Illustrative to" should read --Illustrative of--.

Column 15, line 30 (Claim 34), after "reduced" and before "so", the following should be inserted --portion and the enlarged portion of the head portion--.

Column 16, line 2, (Claim 40), after "body" and before "for", --adapted-- should be inserted.

Column 16, line 4 (Claim 40), after "and" and before "opposite", --an-- should be inserted.

Column 16, line 9, (Claim 40), "of the reduced" should read --and the reduced--.

Column 16, line 16 (Claim 40), "cut" should read --cup--.

Column 17, line e (Claim 48), after "body" and before "for", --adapted-- should be inserted.

UNITED STATES PATENT AND TRADEMARK OFFICE
CERTIFICATE OF CORRECTION

PATENT NO. : 5,334,020
DATED : August 2, 1994
INVENTOR(S) : Ronald C. Eckert

It is certified that error appears in the above-indentified patent and that said Letters Patent is hereby corrected as shown below:

Column 17, line 4 (Claim 48), "end to be" should read --end for--.

Signed and Sealed this

Twenty-second Day of November, 1994

Attest:

BRUCE LEHMAN

*Attesting Officer*   *Commissioner of Patents and Trademarks*